United States Patent [19]
Hibbs et al.

[11] Patent Number: 6,122,056
[45] Date of Patent: Sep. 19, 2000

[54] DIRECT PHASE SHIFT MEASUREMENT BETWEEN INTERFERENCE PATTERNS USING AERIAL IMAGE MEASUREMENT TOOL

[75] Inventors: Michael Straight Hibbs, Westford; Song Peng, South Burlington, both of Vt.

[73] Assignee: International Business Machines Corporation, Armonk, N.Y.

[21] Appl. No.: 09/056,521

[22] Filed: Apr. 7, 1998

[51] Int. Cl.[7] ..................................................... G01B 9/02
[52] U.S. Cl. ............................................. 356/345; 356/354
[58] Field of Search .................................. 356/345, 351, 356/353, 354, 361

[56] References Cited

U.S. PATENT DOCUMENTS

| | | | |
|---|---|---|---|
| 5,576,829 | 11/1996 | Shiraishi et al. | 356/354 |
| 5,604,591 | 2/1997 | Kitagawa | 356/361 |
| 5,898,498 | 4/1999 | Kirk | 356/353 |

OTHER PUBLICATIONS

Ghosh, A.P. and Dove, D.B., "Direct Phase Measurements in Phase Shift Masks," *Spie Proceedings*, Integrated Circuit Metrology, Inspection, and Process Control VI (1992), vol. 1673, pp. 242–254.

Dove, D.B. and Chieu, T.C., "Interferometer for Phase Measurements in Phase Shift Masks," *Proceedings of the Spie*, 12th Annual BACUS Symposium, 1992, vol. 1809, pp. 128–136.

Budd, R.A., et al., "A New tool for Phase Shift Mask Evaluation, the Stepper Equivalent Aerial Image Measurement System—AIMS™," *Spie*, Photomask Technology and Management (1993), vol. 2087, pp. 162–171.

Fujita, Hiroshi, et al., "Accurate Phase Measurement in Phase–Shift Masks with a Differential Heterodyne Interferometer," *Proceedings of the 1994 IEEE Instrumentation and Measurement Technology Conference*, May 10–12, 1994, pp. 683–688.

Chang, F.C., et al., "Measurement of Phase–Shift Masks," *Proceedings of the Spie*, vol. 1926, 1993, pp. 464–471.

Ferguson, R.A., et al., "Impact of Attenuated Mask Topography on Lithographic Performance," *Proceedings of the Spie*, vol. 2197, 1994, pp. 130–139.

Budd, R.A., et al., "A New Mask Evaluation Tool, the Microlithography Simulation Microscope Aerial Image Measurement System," *Proceedings of the Spie*, vol. 2197, 1994, pp. 530–540.

Ferguson, R.A., et al., "Application of Aerial Image Measurement System to Mask Fabrication and Analysis," *Proceedings of the Spie*, Photomask Technology and Management, vol. 2087, 1993, pp. 131–144.

Martino, R., et al., "Application of the Aerial Image Measurement System (AIMS™) to the Analysis of Binary Mask Imaging and Resolution Enhancement Techniques," *Proceedings of the Spie*, vol. 2197, pp. 573–584.

Dove, D.B., and Ghosh, A., "Repair System for Phase Shift Masks," *IBM Technical Disclosure Bulletin*, vol. 36, No. 5, May 1983, pp. 279–280.

*Primary Examiner*—Samuel A. Turner
*Attorney, Agent, or Firm*—Pollock, Vande Sande & Amernick

[57] ABSTRACT

A method of measuring the phase shift between two regions of a phase shift mask. A workpiece is provided including a first pair of slits each having a substantially similar phase shift characteristic and a second pair of slits each having a different phase shift characteristic. Electromagnetic radiation is directed through the first pair of slits and the second pair of slits on the workpiece. A relative shift is measured between interference patterns caused by the first pair of slits and the second pair of slits.

26 Claims, 4 Drawing Sheets

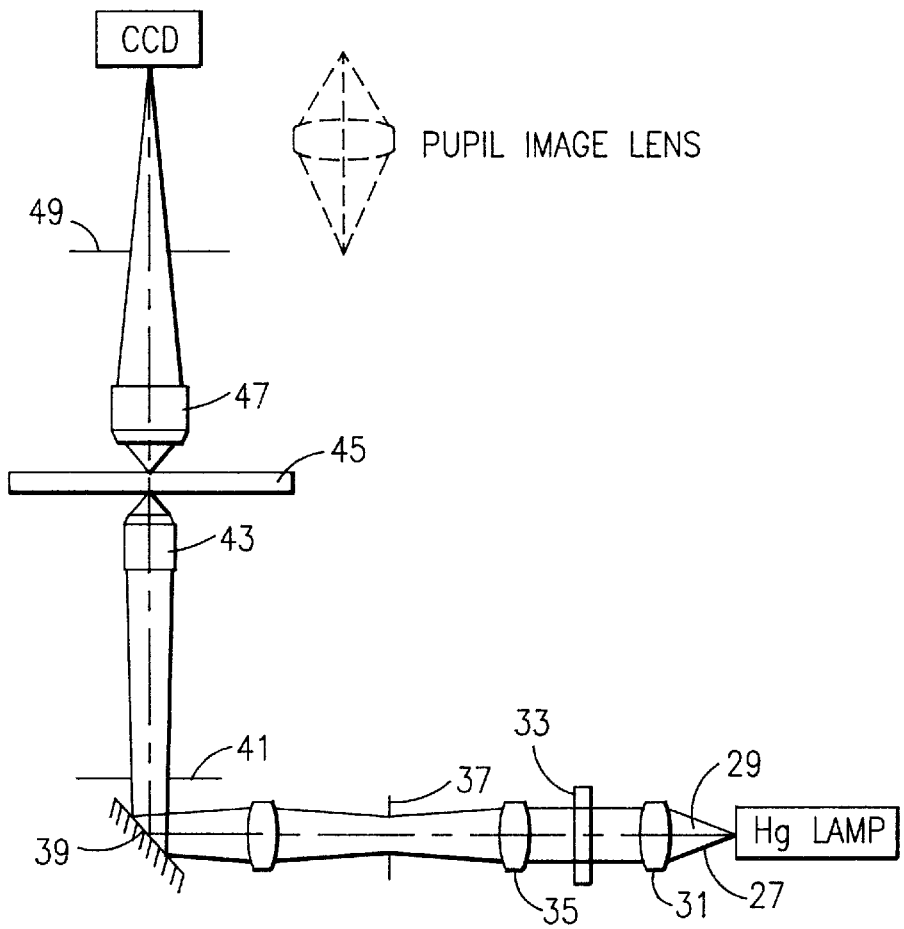
FIG.2c
Prior Art
FIG.2
Prior Art
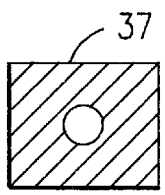
FIG.2b
Prior Art

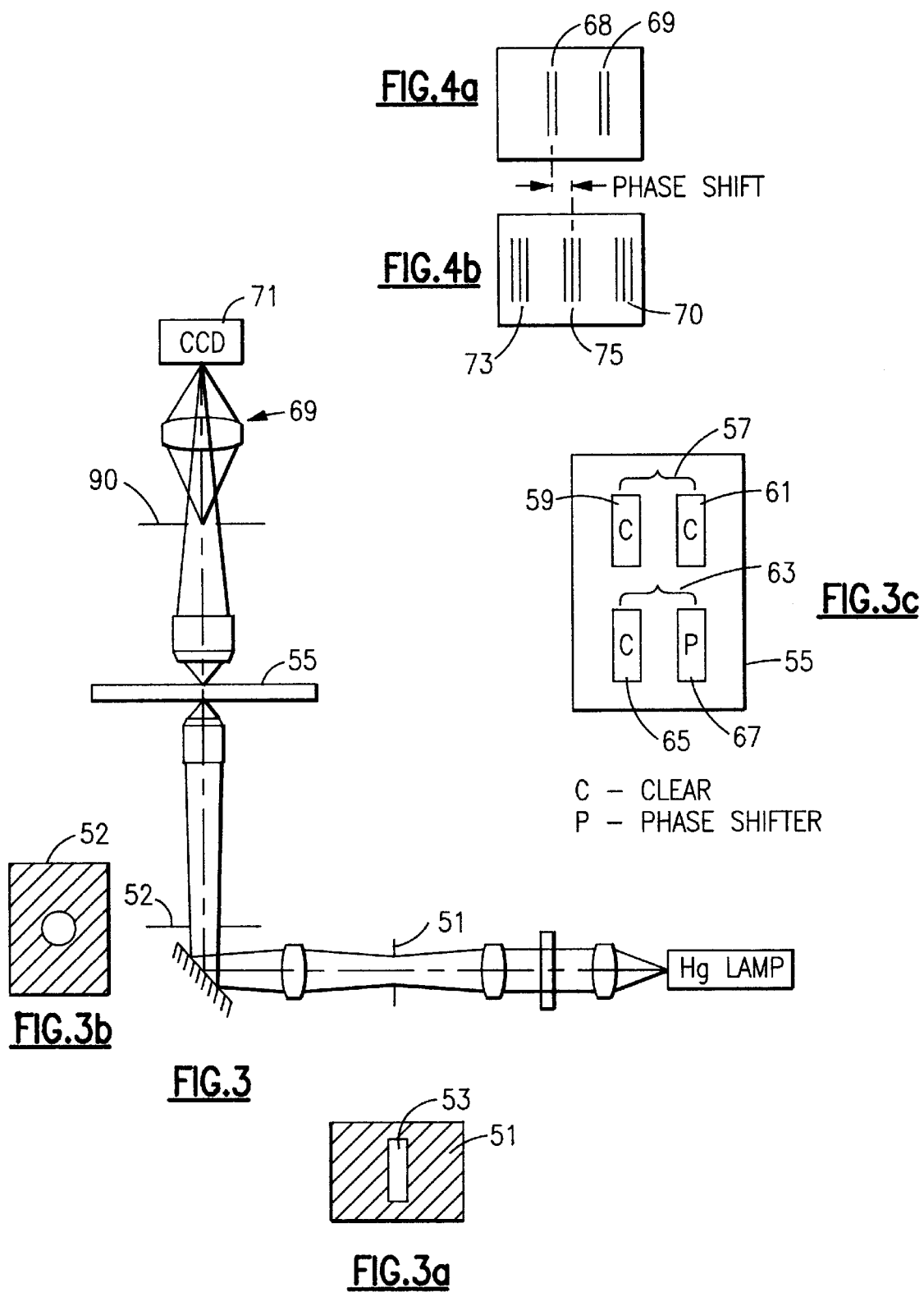

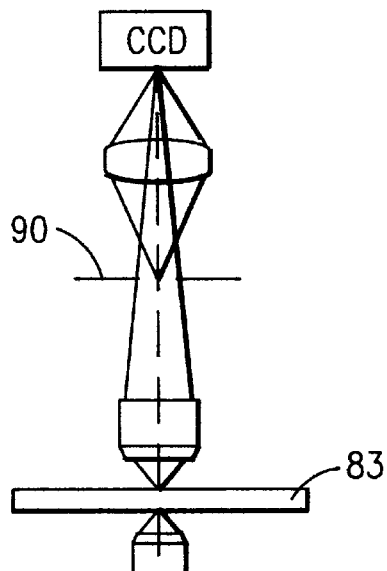
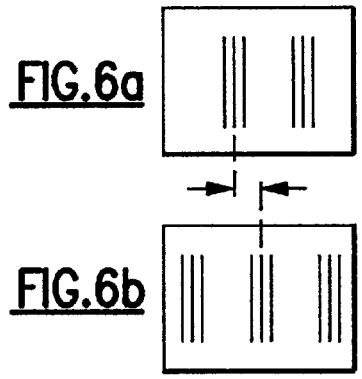
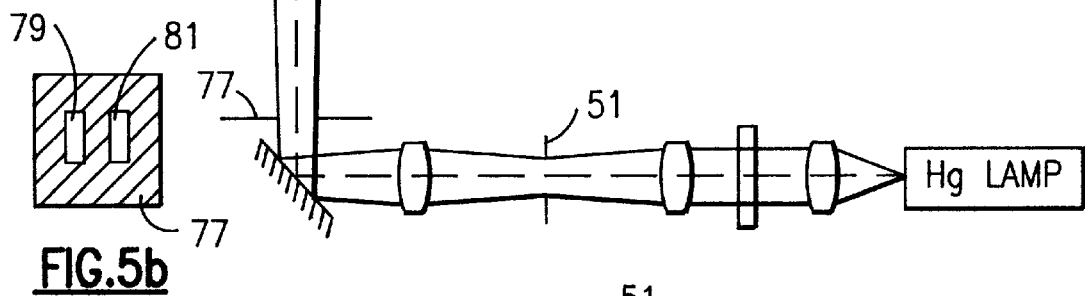
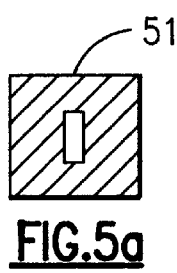
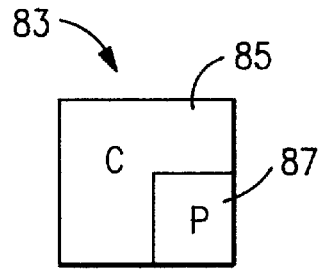

DIRECT PHASE SHIFT MEASUREMENT BETWEEN INTERFERENCE PATTERNS USING AERIAL IMAGE MEASUREMENT TOOL

FIELD OF THE INVENTION

The present invention relates to phase shift masks utilized in the manufacture of very large scale integrated (VLSI) circuit devices. In particular, the present invention is directed to a method and apparatus for measuring the phase shift of various portions of phase shift masks.

BACKGROUND OF THE INVENTION

Very large scale integrated circuit devices typically are manufactured on a substrate, such as a silicon wafer, by a sequence of material additions, such as low pressure chemical vapor depositions, sputtering operations, among others; material removals, such as wet etches, reactive ion etches, among others; and material modifications, such as oxidations, ion implants, among others. Typically, these physical and chemical operations interact with the entire substrate. For example, if a substrate is placed into an acid bath, the entire surface of the substrate will be etched away. In order to build very small electrically active devices on a substrate, the impact of these operations has to be confined to small, well-defined, regions.

Lithography in the context of VLSI manufacturing includes the process of patterning openings in photosensitive polymers, sometimes referred to as "photoresists" or "resists", which define small areas in which substrate material is modified by a specific operation in a sequence of processing steps. The manufacturing of VLSI chips typically involves the repeated patterning of photoresists, followed by etch, implant, deposition, or other operation, and ending with the removal of the exposed photoresist to make way for the new photoresist to be applied for another iteration of this process sequence.

Basic lithography systems typically include a source of light, typically not visible light, a stencil or photomask including a pattern to be transferred to a substrate, a collection of lenses, and a means for aligning existing patterns on the substrate with patterns on the mask or stencil. The aligning may take place in an aligning step or steps and may be carried out with an aligning apparatus. Typically, chips may be processed on a wafer including from 50 to 100 chips. The wafers may be patterned in steps of one to four chips at a time. As a result, such lithography tools are commonly referred to as "steppers".

The resolution of optical projection systems such as lithography steppers is limited by the wavelength, the numerical aperture of the projection optics used in the system, and a constant related to how well a combined lithography system can utilize the theoretical resolution limit in practice. The highest resolution in optical lithography is currently achieved with deep ultraviolet (DUV) steppers operating at 248 nm wavelengths. Mid-ultraviolet (MUV) steppers with a wavelength of 356 nm are also in widespread use.

Conventional photomasks typically consist of chromium patterns on a quartz plate, allowing light to pass wherever the chromium has been removed from the mask. Light of a specific wavelength is projected through the mask onto the photoresist coated substrate, exposing the photoresist wherever chromium has been removed from the mask permitting light to pass through the mask. Exposing the resist to light of the appropriate wavelength causes modifications in the molecular structure of the resist polymers, which permits the use of developer to dissolve and remove the resist in the exposed areas. Resists that act as just described are known as "positive" resists. On the other hand, negative resist systems permit only unexposed areas to be removed by the developer.

Photomasks, when illuminated, can be pictured as an array of individual, infinitely small light sources that can be either turned on, such as areas not covered by chromium or other material, or turned off, such as areas covered by chrome or other material. If the amplitude of the electric field vector that describes the light radiated by these individual light sources is mapped across a cross-section of the mask, a step function will be plotted reflecting the two possible states that each point of the mask can be found, either light on or light off.

Conventional photomasks are commonly referred to as "chrome on glass" (COG) binary masks, due to the binary nature of the image amplitude. The perfectly square step function of binary masks actually exists only in the theoretical level of the exact mask plane. Any distance away from the mask, such as at the substrate plane, diffraction will cause images to exhibit a finite image slope. At small dimensions, that is, when the size and spacing of the images to be printed are small relative to the wavelength and inverse of the numerical aperture, the electric field vectors of adjacent images will interact and add constructively.

Therefore, not only is diffraction a phenomenon that must be addressed when dealing with very small images, interference must also be addressed. The resulting light intensity curve between features is not completely dark, as a result of the diffraction and interference phenomenon. Rather, the light intensity curve exhibits significant amounts of light intensity created by the interaction of adjacent features.

The resolution of an exposure system is limited by the contrast of the projected image, that is, the intensity difference between adjacent light and dark features. An increase in the light intensity in nominally dark regions will eventually cause adjacent features to print as one combined structure rather than as discrete images.

The quality with which small images can be replicated in lithography depends largely on the available process latitude, that is, the amount of allowable dose and focus variation that still results in the correct image size formation. Phase shift mask (PSM) lithography improves the lithographic process latitude by introducing a third parameter on the mask. The third parameter is the electric field vector associated with the light produced by the light source.

The electric field vector, like any vector defined quantity, has a magnitude and direction. Therefore, in addition to turning the electric field amplitude on and off, the electric field vector can be turned on with a phase of about 0°, or with a phase of about 180°. This phase variation is achieved in phase shift masks by modifying the length that a light beam travels through the mask material. By recessing the mask, such as by etching, to an appropriate depth, light traversing the center portion of the mask and light traversing the thinner portion of the mask may be made to be about 180° out of phase. Alternatively, a material, such as a transparent thin film, may be applied to the surface of the mask to accomplish the same difference in traverse distance.

A 180° phase difference means that the electric field vectors of light traversing adjacent portions of the mask should be of about equal magnitude but in substantially opposite directions. As a result, any interaction between light beams passing through the adjacent areas results in substantially perfect cancellation. Greater detail regarding phase shift masks is provided by "Phase-shifting Mask Strategies: Isolated Dark Lines", Mark D. Levinson, *Microlithography World*, March/April 1992, pp. 6–12, the entire contents of which are hereby incorporated by reference.

As can be appreciated from the above discussion, it is important to verify the nature of the shifting caused by the phase shift mask. In other words, it is important to measure the magnitude and direction of the phase shift. Currently, phase angle can be measured using dedicated interferometers. FIG. 1 shows an example of an apparatus that may be utilized in measuring phase angle on a phase shift mask.

Utilization of an apparatus such as that shown in FIG. 1 is described, for example, in "Direct Phase Measurements in Phase Shift Masks", A. P. Ghosh and D. B. Dove, *SPIE*, Vol. 1673, Integrated Circuit Metrology, Inspection, and Process Control VI (1992); "Interferometer for Phase Measurements in Phase Shift Masks", Derek B. Dove, Trieu C. Chieu, and Amal P. Ghosh, *SPIE*, Vol. 1809, 12th Annual BACUS Symposium (1992); "A New Tool for Phase Shift Mask Evaluation, the Stepper Equivalent Aerial Image Measurement System—AIMS™", Russell A. Budd, John Staples, and Derek Dove, *SPIE*, Vol. 2087, Photomask Technology and Management (1993), "Accurate Phase Measurement in Phase-Shift Masks with a Differential Heterodyne Interferometer", Hiroshi Fujita, et al., *Proceedings of the 1994 IEEE Instrumentation and Measurement Technology Conference*, Part 2, IMTC May 10–12, 1994 Hamamatsu, pp. 683–688; "Measurement of Phase-Shift Masks", F. C. Chang, et al., SPIE, Vol 1926, pp. 464–471, 1993; "Impact of Attenuated Mask Topography on Lithographic Performance", Richard A. Ferguson, et al., *SPIE*, Vol. 2197, pp. 130–139, 1994; "A New Mask Evaluation Tool, the Microlithography Simulation Microscope Aerial Image Measurement System", R. A. Budd, et al., *SPIE*, Vol. 2197, pp. 530–540, 1994; "Application of an Aerial Image Measurement System to Mask Fabrication and Analysis", Richard A. Ferguson, et al., *SPIE*, Vol. 2087, Photomask Technology and Management (1993), pp. 131–144; "Application of the Aerial Image Measurement System (AIMS™) to the Analysis of Binary Mask Imaging and Resolution Enhancement Techniques," R. Martino, et al., *SPIE*, Vol. 2197, pp. 573–584, 1994; and "Repair System for Phase Shift Masks," D. B. Dove and A. Ghosh, *IBM Technical Disclosure Bulletin*, Vol. 36, No. 05, May 1993, pp. 279–280; the entire disclosures of all of the above are hereby incorporated by reference.

Measurement of the actual phase shift typically is necessary to ensure that the physical structure created on the mask to cause the phase shift corresponds to the actual image that is desired to be projected upon the photoresist. Such verification is also necessary to ensure that the proper exposure is applied to the photoresist. Additionally, currently, phase shift masks are typically developed by computer programs that permit the image projected on the photoresist to be calculated from the above-discussed variables. The actual fabricated masks may contain small errors that may not be recognized or may be difficult to model. Hence, the reason for developing apparatus and method to measure the actual phase shift.

SUMMARY OF THE INVENTION

An object and advantage of the present invention is to provide a method and apparatus for directly measuring phase shifting produced by phase shift areas of phase shift masks.

Accordingly, aspects of the present invention provide a method of measuring the phase shift between two regions of a phase shift mask. The method includes providing a workpiece including a first pair of slits. Each slit of the first pair of slits has a substantially similar phase shift characteristic. The workpiece is also provided with a second pair of slits. Each slit of the second pair of slits has a different phase shift characteristic. Electromagnetic radiation is directed through the first pair of slits and the second pair of slits on the workpiece. A relative shift between interference patterns caused by the first pair of slits and the second pair of slits is measured to determine the phase shift between the two slits of the second pair of slits.

Aspects of the present invention also provide a method of measuring phase shift between two regions of a phase shift mask that includes providing a workpiece including a first transparent region and a second transparent region having a different phase shift characteristic than the first transparent region. A first aperture is provided that includes a pair of slits having substantially similar phase shift characteristics. Electromagnetic radiation is directed through the slits in the aperture and then through the workpiece, such that the electromagnetic radiation passing through one of the slits passes through the first transparent region and electromagnetic radiation passing through the other of the slits passes through the second transparent region. A relative shift between interference patterns caused by the electromagnetic radiation passing through the pair of slits and the workpiece is measured.

According to additional aspects, the present invention provides an apparatus for measuring the phase shift between two regions of a phase shift mask. The apparatus includes a workpiece including a first pair of slits. Each slit of the first pair of slits has a substantially similar phase shift characteristic. The workpiece also includes a second pair of slits. Each slit of the second pair of slits has a different phase shift characteristic. A source of electromagnetic radiation is provided that may be directed through the first pair of slits and the second pair of slits on the workpiece. The apparatus also includes means for measuring a relative shift between interference patterns caused by the first pair of slits and the second pair of slits.

Further aspects of the present invention provide an apparatus for measuring phase shift between two regions of a phase shift mask. The apparatus includes a workpiece including a first transparent region and a second transparent region having a different phase shift characteristic than the first transparent region. A first aperture includes a pair of slits having substantially similar phase shift characteristics. The apparatus also includes a source of electromagnetic radiation directed through the slits in the aperture and then through the workpiece, such that electromagnetic radiation passing through one of the slits passes through the first transparent region and electromagnetic radiation passing through the other of the slits passes through the second transparent region. The apparatus also includes means for measuring the interference patterns caused by electromagnetic radiation passing through the pair of slits and the workpiece.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

FIG. 2 provides a schematic view of a known tool for conducting aerial image measurements in phase shift masks;

FIG. 2b represents a plan view of the sigma aperture included in the apparatus shown in FIG. 2;

FIG. 2c represents a plan view of a field aperture included in the apparatus shown in FIG. 2;

FIG. 3 represents a schematic view of an embodiment of an apparatus according to the present invention for conducting phase measurements in phase shift masks;

FIG. 3a represents a plan view of the sigma aperture included in the apparatus shown in FIG. 3;

FIG. 3b represents a plan view of the field aperture that may be included in the apparatus shown in FIG. 3;

FIG. 3c represents a plan view of the mask that may be included in the embodiment of the apparatus shown in FIG. 3;

FIG. 4a and FIG. 4b represent a view of images imaged by the camera in the embodiment of the apparatus shown in FIG. 3 as a result of radiation passing through the apparatus shown in FIG. 3;

FIG. 5 represents another embodiment of an apparatus according to the present invention for conducting phase measurements in phase shift masks;

FIG. 5a represents a plan view of the sigma aperture included in the apparatus shown in FIG. 5;

FIG. 5b represents a plan view of the field aperture that may be included in the apparatus shown in FIG. 5;

FIG. 5c represents a plan view of the mask that may be included in the embodiment of the apparatus shown in FIG. 5; and FIG. 6a and FIG. 6b represent a view of images imaged by the camera in the embodiment of the apparatus shown in FIG. 5 as a result of radiation passing through the apparatus shown in FIG. 5.

DETAILED DESCRIPTION OF THE INVENTION

Figure 1:
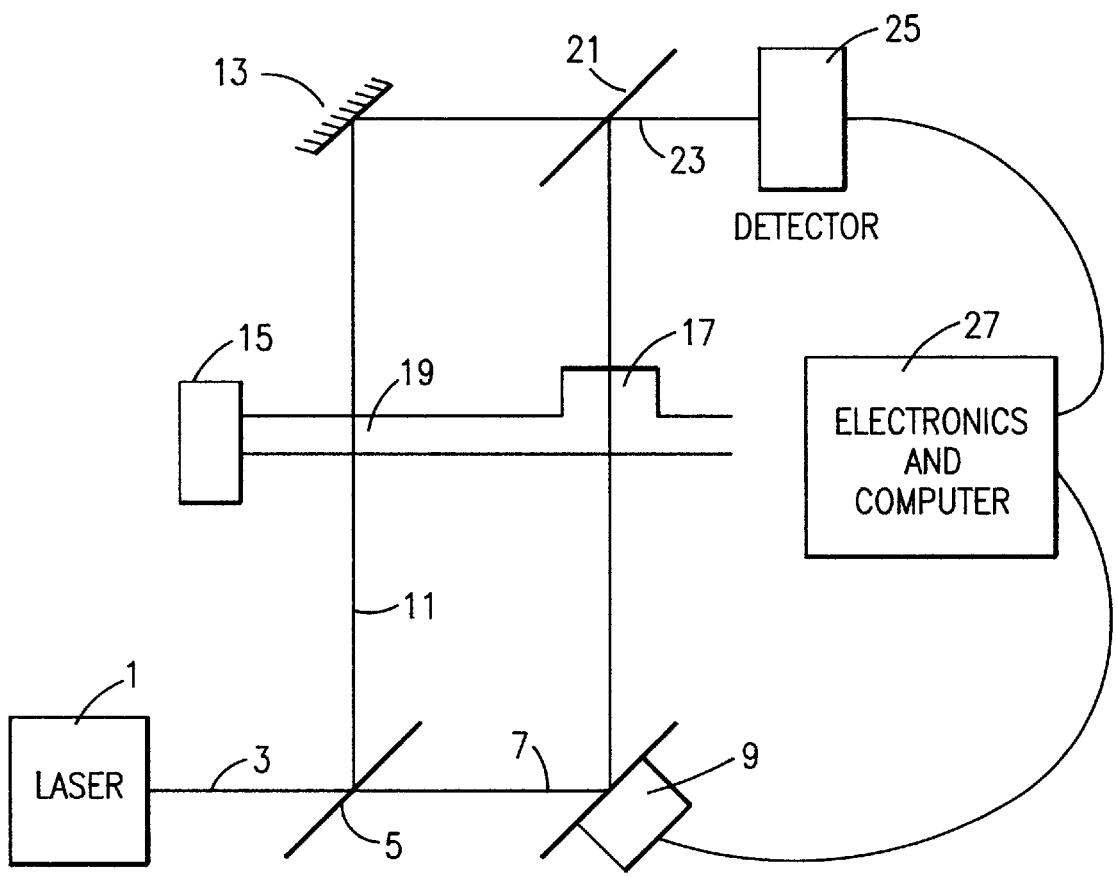
FIG. 1 represents a schematic view of a known apparatus for conducting phase measurements in phase shift masks.

As stated above, the present invention provides a method and apparatus for making phase measurements of various regions in phase shift masks. FIG. 1 shows an embodiment of a known system for conducting phase measurements in phase shift masks. This apparatus utilizes interferometers to measure the phase shift characteristics.

The apparatus shown in FIG. 1 includes a laser 1. The laser produces a beam 3. The beam 3 is directed to a beam splitter 5. One of the beams 7, produced by beam splitter 5, is directed to phase modulator 9. The other beam 11, produced by beam splitter 5, is directed toward a mirror 13. Both beams 7 and 11 produced by beam splitter 5 pass through a phase shift mask 15. One beam 7 passes through a phase shifted region 17 of the mask 15, while the other beam 11 passes through the un-phase shifted portion 19 of the mask 15. The beam 11 then bounces off mirror 13 and through beam splitter 21. Beam 17 passes through the mask 15 and then onto beam splitter 21. All of the beams are ultimately recombined after the beam splitter into one beam 23 that impacts upon detector 25. Electronics and computer 27 are used in the apparatus shown in FIG. 1 to control the phase modulator 9 for interacting with beam 7. The electronics and computer 27 also analyze the beam 23 impacting upon detector 25. The apparatus shown in FIG. 1 utilizes detected interference signal to make the phase shift measurements.

FIG. 2 shows an embodiment of a known apparatus that may serve as the basis for an apparatus according to the present invention for directly making phase measurements in phase shift masks. The present apparatus modifies this apparatus as described below to permit phase shift characteristics to be directly measured. The methods of the present invention utilize this modified apparatus.

The device shown in FIG. 2 includes a source of electromagnetic radiation 27. One example of a source of electromagnetic radiation is a mercury lamp. The source of electromagnetic radiation 27 generates electromagnetic radiation 29. Another example of a radiation source is a high pressure arc lamp. The radiation passes through lens 31.

A filter 33 may be located downstream of lens 31. The filter may filter out all wavelengths except for those that would be utilized when exposing photoresist with the phase shift mask being analyzed. Examples of filters that may be utilized in the apparatus shown in FIG. 2 are narrow band dichroic filters. Preferably, the filter system is designed to avoid subjecting the filters to thermal shock from the radiation source, which can shorten filter life.

After passing through the filter, the radiation may be directed through another lens 35 that focuses the beam toward an aperture 37. A cross-section of the aperture is shown in FIG. 2b.

The numerical aperture of the apparatus shown in FIG. 2 preferably is set to duplicate the numerical aperture of the stepper on the imaging side of the stepper lens so as to reproduce resolution characteristics of the stepper.

The filter permits adjustment of a second parameter related to coherence of the illumination. The coherence of the illumination typically is described in terms of a pupil-filling factor, or sigma value. The size of the aperture 37 may be varied to set the pupil-filling factor sigma to substantially correspond to that of a particular stepper.

The illumination in the apparatus may also be modified to provide uniform illumination across the aperture 37. This modification may be performed by lenses 31 and/or 35. Preferably, the illumination is modified so as to still permit sufficient lighting through the system to ensure camera exposures of typically less than 1 second.

Downstream of the aperture 37, a lens may be introduced to focus the image on a camera sensitive to the wavelengths of radiation transmitted through the apparatus. The amount of magnification may vary. According to one example, the lens magnifies the image more than about 200 times, compared with the mask.

The radiation may then be bounced off angled surface 39 and passed through field aperture 41. FIG. 2c shows one example of a cross-section of a field aperture that may be included in such an apparatus. In the aerial image measurement system the function of this field aperture may simply limit the field of view of the system. The field aperture 41 is imaged onto the mask by condenser lens 43. The radiation may then pass through condenser 43 prior to passing through mask 45. After passing through mask, the radiation may pass to objective 47. Next, the radiation passes through aperture 49. Aperture 49 may be similar to the aperture utilized in the exposure system to be utilized with the mask.

The objective 47 images the mask through the NA aperture to the image plane where the CCD camera sits. The pupil image lens 50 typically is not directly used in the aerial image measurement process, but it is used to align the NA aperture 49. However, during an alignment procedure the lens 50 may be inserted into the optical path. On the other hand, during aerial image measurement the lens 50 may be out of the optical path. As described herein, the lens 50 may be used during direct phase measurement.

The radiation may then be imaged by a detector, such as a camera. If a camera is used, the camera preferably is a CCD camera. Additionally, the camera preferably is sufficient to detect the radiation and permit analysis of the alteration of the radiation by the mask.

The apparatus shown in FIG. 2 may be modified to produce an apparatus according to the present invention. FIG. 3 shows one embodiment of an apparatus according to the present invention for directly measuring phase angle on phase shift masks. As can be seen, the sigma aperture 53 in the embodiment shown in FIG. 3a has a rectangular cross-section, as opposed to the circular cross-section in the prior art apparatus shown in FIG. 2. However, there is no requirement that the aperture have such a cross-section.

The sigma aperture 53 typically has a small size along a direction that is perpendicular to reference pair of slits 57 and the measurement pair of slits 63. The purpose of this arrangement is to provide high coherence illumination to enhance the interference signal. Along the other direction, the sigma aperture 53 may have larger size so as to collect enough illumination power. FIG. 3b shows a cross-sectional view of an embodiment of a field aperture that may be included in the apparatus shown in FIG. 3.

An additional difference between the present, as shown in FIG. 3, and the prior art apparatus shown in FIG. 2 may include the mask that the radiation passes through prior to being imaged by the camera may include two different pairs of slits. FIG. 3c shows a cross-sectional view of the mask included in the apparatus shown in FIG. 3. In the embodiment shown in FIG. 3, the mask includes a reference pair of slits. Each slit in the reference pair includes substantially the same phase characteristics. In the embodiment shown in FIG. 3, both slits in the reference pair of slits are clear, without any phase shift.

The mask and embodiment shown in FIG. 3 also includes a measurement pair of slits. Each slit in the measurement pair of slits includes a different phase shift characteristic. In the embodiment shown in FIG. 3, one slit of the measurement pair is clear, without any phase shift characteristics. The other slit of the measurement pair of slits includes a phase shift. The phase shift slit in the measurement pair may vary depending upon the mask being evaluated. Additionally, the way that the phase shift is created, such as whether it is created by etching the mask or depositing material on the mask may also vary.

Although each slit in the reference pair of slits and one slit of the measurement pair of slits are each clear, these three slits may have a similar phase shift characteristic that is different from the other slit of the measurement pair of slits.

The distance separating the reference pair of slits 57 and the measurement pair of slits 63 typically is sufficient so that when one pair of slits is inside the image of the field aperture the other one is outside the image. The separation of the slits typically permits a sufficient number of fringes to form on the CCD camera. The width of the slits typically is at least 5 times smaller than the distance separating the two slits in either the reference pair or the measurement pair.

An additional difference between the embodiment of the present invention shown in FIG. 3 and the embodiment of a prior art apparatus shown in FIG. 2 is that the present invention, as shown in FIG. 3, may include a pupil image lens 69. The pupil image lens 69 images the plane of the NA aperture to the CCD camera. The objective lens projects the Yong's interference fringes generated by the slit pair onto the NA aperture plane. Consequently, the pupil image lens projects these fringes onto the CCD camera.

After passing through the pupil image lens, the radiation pattern is then imaged by the camera 71. The camera included in the apparatus of the present invention may have the same characteristics as described above for the prior art apparatus shown in FIG. 2.

Preferably, the radiation produced by radiation source is substantially similar to the radiation that would be utilized in a mask that includes phase shift region such as that in the slit 67 included in the measurement pair 63 in mask 55. The radiation passing through the apparatus shown in FIG. 3 typically produces images such as those shown in FIG. 4. These are created by the radiation passing through the reference pair slits and the measurement pair slits.

FIG. 4 shows the interference patterns resulting from radiation passing through a pair of slits having similar phase shift characteristics, such as the reference pair of slits 57, and radiation passing through slits having different phase shift characteristics, such as the measurement pair 63. The distance between similar regions of the images shown in FIG. 4 is measured to determine the relative phase angles of the two slits of the reference pair of slits.

The distance between two adjacent fringes in either FIG. 4a or FIG. 4b typically corresponds to a 360 degree phase. Thus, by measuring the relative fringe shift between the measurement pair and the reference pair, the phase difference between the two slits of the measurement pair can be determined. The phase angle is linearly proportional to the relative fringe shift. In practical implementation, the fringe shift can be calculated using various digital signal processing techniques including auto-correlation.

FIG. 5 shows another embodiment of an apparatus according to the present invention. As can be seen in FIG. 5, a difference between the apparatus shown in FIG. 3 and the apparatus shown in FIG. 5 is that the field aperture 77 in the embodiment shown in FIG. 5 includes two slits. The two slits 79 and 81 may be imaged onto the mask by the condenser lens. The purpose of these slits is to replace the slit pairs 55 and 67 described above. In the embodiment including slits 79 and 81 the mask needs only a transition edge to facilitate the phase measurement. The separation of the slits on the field aperture preferably permits enough number of fringes form on the CCD camera. FIG. 5b shows a cross-section of the embodiment of the field aperture shown in FIG. 5.

A further difference between the embodiment of the invention shown in FIG. 5 and the embodiment shown in FIG. 3 is that the mask 83 in the embodiment shown in FIG. 5 includes two areas of different phase characteristics. FIG. 5c shows a cross-section of the embodiment of the mask shown in FIG. 5. In the embodiment shown in FIG. 5 and FIG. 5c, the mask 83 includes two areas having different phase shift characteristics. The mask shown in FIG. 5c includes a clear area 85 and a phase shifted area 87. Preferably, the mask includes a clear area and a phase shifted area since the clear area has no phase shift characteristics. According to other embodiments, the mask 83 may simply have two areas, both of which are phase shifted, each with a different phase shift characteristic.

As can be seen in FIG. 5, the phase shift accomplished by the two different pairs of slits in the mask in the embodiment shown in FIG. 3 is accomplished by the two slits in the field aperture and the two areas of different phase shift characteristic in the embodiment shown in FIG. 5. Just as with the embodiment shown in FIG. 3, the embodiment shown in FIG. 5 produces two images produced by radiation passing through the two slits of the field aperture and the two areas with different phase shift characteristics in the mask. Once again, the phase shift can be determined by measuring the difference between the interference patterns in the images shown in FIG. 6a and FIG. 6b.

Advantages of the present invention include utilizing an existing tool, the aerial image measurement system, for measuring phase, although this tool is modified to produce the apparatus of the present invention. Additionally, an advantage of the present invention is that it utilizes the pupil image lens for frequency-plan imaging. Additionally, the present invention utilizes slit apertures on the sigma-aperture plane. Furthermore, the present invention utilizes reference slits and measurement slits on a mask, double slits in the field aperture, and algorithms for extracting phase angle information.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A method of measuring the phase shift between two regions of a phase shift mask, said method comprising the steps of:

providing a workpiece including a first pair of slits each having a substantially similar phase shift characteristic and a second pair of slits each of said second pair of slits having a different phase shift characteristic;

directing electromagnetic radiation through said first pair of slits and said second pair of slits on said workpiece; and directly measuring a relative shift between interference patterns caused by said first pair of slits and said second pair of slits.

2. The method according to claim 1, further comprising the steps of:

providing at least one aperture situated between a source of said electromagnetic radiation and means for measuring said relative shift; and providing at least one lens situated between said source of electromagnetic radiation and said measuring means.

3. The method according to claim 1, wherein said relative shift is measured by a CCD camera and said method further comprises the step of providing a pupil image lens through which the electromagnetic radiation passes after passing through the workpiece and prior to being imaged on the CCD camera.

4. A method of measuring the phase shift between two regions of a phase shift mask, said method comprising the steps of:

providing a workpiece including a first transparent region and a second transparent region having a different phase shift characteristic than said first transparent region;

providing a first aperture including a pair of slits having substantially similar phase shift characteristics;

directing electromagnetic radiation through said slits in said aperture and then through said workpiece, such that electromagnetic radiation passing through one of said slits passes through said first transparent region and electromagnetic radiation passing through the other of said slits passes through said second transparent region; and directly measuring a relative shift between interference patterns caused by electromagnetic radiation passing through said pair of slits and said workpiece.

5. The method according to claim 4, further comprising the steps of:

providing at least one additional aperture situated between a source of said electromagnetic radiation and means for measuring said relative shift; and providing at least one lens situated between said source of electromagnetic radiation and said measuring means.

6. The method according to claim 4, wherein said said relative shift is measured with a CCD camera and said method further comprises the step of providing a pupil image lens through which the electromagnetic radiation passes after passing through the workpiece and prior to being imaged on the CCD camera.

7. An apparatus for measuring the phase shift between two regions of a phase shift mask, comprising:

a workpiece including a first pair of slits each having a substantially similar phase shift characteristic and a second pair of slits each of said second pair of slits having a different phase shift characteristic;

a source of electromagnetic radiation that may be directed through said first pair of slits and said second pair of slits on said workpiece; and means for directly measuring a relative shift between interference patterns caused by said first pair of slits and said second pair of slits.

8. The apparatus according to claim 7, wherein said source of electromagnetic radiation is a source of visible light.

9. The apparatus according to claim 7, wherein said source of electromagnetic radiation is a mercury lamp.

10. The apparatus according to claim 7, further comprising:

a filter transmitting electromagnetic radiation having wavelengths of about 248 nm and about 365 nm.

11. The apparatus according to claim 7, further comprising:

at least one aperture situated between said source of electromagnetic radiation and said measuring means; and at least one lens situated between said source of electromagnetic radiation and said measuring means.

12. The apparatus according to claim 7, wherein said measuring means is a CCD camera and said apparatus further comprises a pupil image lens through which the electromagnetic radiation passes after passing through the workpiece and prior to being imaged on the CCD camera.

13. An apparatus for measuring the phase shift between two regions of a phase shift mask, comprising:
  a workpiece including a first transparent region and a second transparent region having a different phase shift characteristic than said first transparent region;
  a first aperture including a pair of slits having substantially similar phase shift characteristics;
  a source of electromagnetic radiation that may be directed through said slits in said aperture and then through said workpiece, such that electromagnetic radiation passing through one of said slits passes through said first transparent region and electromagnetic radiation passing through the other of said slits passes through said second transparent region; and
  means for directly measuring a relative shift between interference patterns caused by electromagnetic radiation passing through said pair of slits and said workpiece.

14. The apparatus according to claim 13, wherein said source of electromagnetic radiation is a source of visible light.

15. The apparatus according to claim 13, wherein said source of electromagnetic radiation is a mercury lamp.

16. The apparatus according to claim 13, further comprising:
  a filter transmitting electromagnetic radiation having wavelengths of about 248 nm and about 365 nm.

17. The apparatus according to claim 13, further comprising:
  at least one additional aperture situated between said source of electromagnetic radiation and said measuring means; and
  at least one lens situated between said source of electromagnetic radiation and said measuring means.

18. The apparatus according to claim 13, wherein said measuring means is a CCD camera and said apparatus further comprises a pupil image lens through which the electromagnetic radiation passes after passing through the workpiece and prior to being imaged on the CCD camera.

19. The method according to claim 1, wherein the relative shift is measured in the pupil plane.

20. The method according to claim 19, wherein the relative shift is measured as a lateral shift of the interference patterns.

21. The method according to claim 4, wherein the relative shift is measured in the pupil plane.

22. The method according to claim 21, wherein the relative shift is measured as a lateral shift of the interference patterns.

23. The apparatus according to claim 7, wherein the apparatus measures relative shift in the pupil plane.

24. The apparatus according to claim 23, wherein apparatus measures the relative shift as a lateral shift of the interference patterns.

25. The apparatus according to claim 13, wherein the apparatus measures relative shift in the pupil plane.

26. The apparatus according to claim 25, wherein apparatus measures the relative shift as a lateral shift of the interference patterns.

* * * * *